United States Patent [19]

Mistretta et al.

[11] 4,204,226

[45] May 20, 1980

[54] REAL-TIME DIGITAL X-RAY TIME INTERVAL DIFFERENCE IMAGING

[75] Inventors: Charles A. Mistretta; Robert A. Kruger; Theodore L. Houk, all of Madison, Wis.

[73] Assignee: Wisconsin Alumni Research Foundation, Madison, Wis.

[21] Appl. No.: 906,631

[22] Filed: May 16, 1978

[51] Int. Cl.² .............................................. H04N 5/32
[52] U.S. Cl. ............................. 358/111; 250/416 TV
[58] Field of Search ....................... 358/105, 111, 106; 250/314, 320, 366, 363 S, 416 TV

[56] References Cited

U.S. PATENT DOCUMENTS

| | | | |
|---|---|---|---|
| 3,265,892 | 8/1966 | Sheldon | 358/111 |
| 3,854,049 | 12/1974 | Mistretta et al. | 250/402 |
| 3,894,181 | 7/1975 | Mistretta et al. | 358/111 |
| 3,974,386 | 8/1976 | Mistretta et al. | 358/111 |
| 4,112,463 | 9/1978 | Kamin | 358/105 |

OTHER PUBLICATIONS

Brennecke et al., A Digital System for Roentgen-Video Image Processing edited by Heintzen and Bursch, George Theime Pub., Stuttgart, 1978, Roentgen-Video Techniques for Dynamic Studies of Structure and Function of the Heart and Circulation, 2nd Int. Workshop Conf., Apr. 1976, pp. 151-157.
Baily et al., Capabilities of a Single Scan TV Radiographic System for Digital Data Acquisition, Investigative Radiology, Jul.-Aug. 1971, pp. 273-279.
Bailey et al., Fluoroscopic Tomography, Investigative Radiology, vol. 9, #2, Mar.-Apr. 1974, pp. 94-103.
Robb et al., 3 Dimensional Reconst. and Display of the Heart, Lungs and Circulation by Multiplanar X-ray Scanning Video Densitometry-Cardiovascular Imaging and Image Processing, SPIE Publication edited by Harrison et al., 1975, pp. 183-194.
Gilbert et al., A Real Time Hardware System for Digital Processing of Wideband Video Images, IEEE Trans. on Computers, vol. C25, #11, Nov. 1976, pp. 1087-1100.

Primary Examiner—Robert L. Griffin
Assistant Examiner—Joseph A. Orsino, Jr.
Attorney, Agent, or Firm—Burmeister, York, Palmatier, Hamby & Jones

[57] ABSTRACT

Difference images, derived from an X-ray image of an anatomical subject, are produced in real time by directing X-rays through an anatomical subject to produce an X-ray image, converting the X-ray image into a series of television fields comprising trains of analog video signals, converting the analog video signals into corresponding digital video signals, integrating the digital video signals over a series of successive time intervals corresponding with a plurality of television fields and thereby producing a series of sets of integrated digital video signals, performing a series of subtractions between each set of integrated video signals and the preceding set of integrated video signals and thereby producing a series of successive digital difference video signals, converting the digital difference video signals into analog difference video signals, and converting the analog difference video signals into a series of visible television difference images representing changes in the X-ray image between the successive time intervals. Apparatus for carrying out this method is also disclosed.

35 Claims, 3 Drawing Figures

FIG. 3

| IMAGE | TV FIELDS | MEMORY 1 | MEMORY 2 | MEMORY 3 | DIFFERENCE IMAGE |
|---|---|---|---|---|---|
| $I_1$ | 1-4 e.g. | INTEGRATE | — | — | — |
| $I_2$ | 5-8 e.g. | OUTPUT: ADD | INTEGRATE | — | — |
| $I_3$ | 9-12 e.g. | OUTPUT: SUBTRACT | OUTPUT: ADD | INTEGRATE | $I_2 - I_1$ |
| $I_4$ | 13-16 e.g. | INTEGRATE | OUTPUT: SUBTRACT | OUTPUT: ADD | $I_3 - I_2$ |
| $I_5$ | 17-20 e.g. | OUTPUT: ADD | INTEGRATE | OUTPUT: SUBTRACT | $I_4 - I_3$ |
| $I_6$ | 21-24 e.g. | OUTPUT: SUBTRACT | OUTPUT: ADD | INTEGRATE | $I_5 - I_4$ |

ETC.

REAL-TIME DIGITAL X-RAY TIME INTERVAL DIFFERENCE IMAGING

The Government has rights in this invention pursuant to Grant No. APR 76-19076 and IPA No. 0001 awarded by the National Science Foundation.

This invention relates to a real-time digital X-ray difference imaging method and apparatus, which will find many applications in making diagnostic X-ray studies of humans and animals, but are particularly well adapted for visualizing the cardiovascular system, including the heart and any blood vessels which are of interest. This invention is able to produce a series of continuous television images, showing the circulation of the blood in any desired portion of the cardiovascular system. Thus, the present invention is extremely valuable for visualizing the motion of the heart in real time, and for showing the circulation of the blood in the arteries and veins which are associated with the heart. This invention is also very advantageous for making X-ray studies of the abdomen and the brain. For example, the present invention may be employed very advantageously for showing the circulation of the blood in the renal arteries and veins, associated with the kidneys, and in the carotid arteries and veins in the neck and head.

One object of the present invention is to produce television difference images, in which the circulating blood is shown with greatly enhanceed visibility, while image elements due to bone and soft tissue are largely eliminated by subtraction.

A further object is to produce television difference images in which the visibility of an X-ray contrast medium is enhanced to such a great extent that the contrast medium can be injected into one or more peripheral veins in the arms or legs of the patient, without any need to insert a catheter, as in prior procedures.

Another object is to produce television difference images, whereby the circulated blood is visualized to a useful extent, without utilizing any contrast medium.

Generally, the present invention provides a method of producing visible difference images derived from an X-ray image of an anatomical subject, such method comprising the steps of directing X-rays through an anatomical subject to produce an X-ray image, converting the X-ray image into a series of television fields comprising trains of analog video signals, converting such analog video signals into corresponding digital video signals, integrating the digital video signals over a series of successive time intervals corresponding with a plurality of television fields and thereby producing a series of sets of integrated digital video signals, performing a series of subtractions between each set of integrated video signals and the preceding set of integrated video signals and thereby producing a series of successive digital difference video signals, converting said digital difference video signals into analog difference video signals, and converting said analog difference video signals into a series of visible television difference images representing changes in the X-ray image between the successive time intervals.

An X-ray contrast medium may be introduced into the anatomical subject with a timing such that movement of the contrast medium in the subject will occur during the series of television fields.

Filtration of the X-rays may be employed to enhance the visibility of the X-ray contrast medium. The X-ray contrast medium may be of a type containing iodine. In that case, an X-ray filter containing cerium may be employed to enhance the visibility of the iodine.

The analog video signals are preferably amplified logarithmically, prior to the conversion of the analog video signals to digital video signals.

To carry out this method, the present invention provides diagnostic anatomical X-ray apparatus, comprising means including an X-ray source for producing an anatomical X-ray image, television means for converting the X-ray image into a series of television fields comprising trains of analog video signals, an analog-to-digital converter for converting the analog video signals into corresponding digital video signals, three memory systems for successively storing the digital video signals, cyclical means for successively supplying the digital video signals to the three memory systems in rotation for successive first, second and third time intervals, each of the memory systems comprising a digital memory having a capacity corresponding to at least one television field and integrating means for causing the digital memory to integrate the digital video signals over a predetermined number of television fields for the corresponding time interval, subtracting means for producing digital difference video signals by performing a subtraction between the two sets of integrated digital video signals stored in the most recently filled memory system and the previously filled memory system during the time interval when the other memory system is being filled, a digital-to-analog converter for converting said digital difference video signals into analog video signals, and means including a television display device for producing visible difference images corresponding to the analog X-ray image between the successive time intervals.

The apparatus may include means for establishing each of the time intervals so as to be a few television fields, on the order of four television fields, for example.

X-ray filtration means may be employed between the X-ray source and the television means for enhancing the visibility of a predetermined X-ray contrast medium. The X-ray filtration means may contain cerium for enhancing the visibility of an X-ray contrast medium containing iodine.

The apparatus may include a logarithmic amplifier for logarithmically amplifying the analog video signals for presentation to the analog-to-digital converter.

Further objects, advantages and features of the present invention will appear from the following description, taken with the accompanying drawings, in which:

FIG. 3 is a table illustrating details of the construction and operation of the apparatus of FIGS. 1 and 2.

Figure 1:
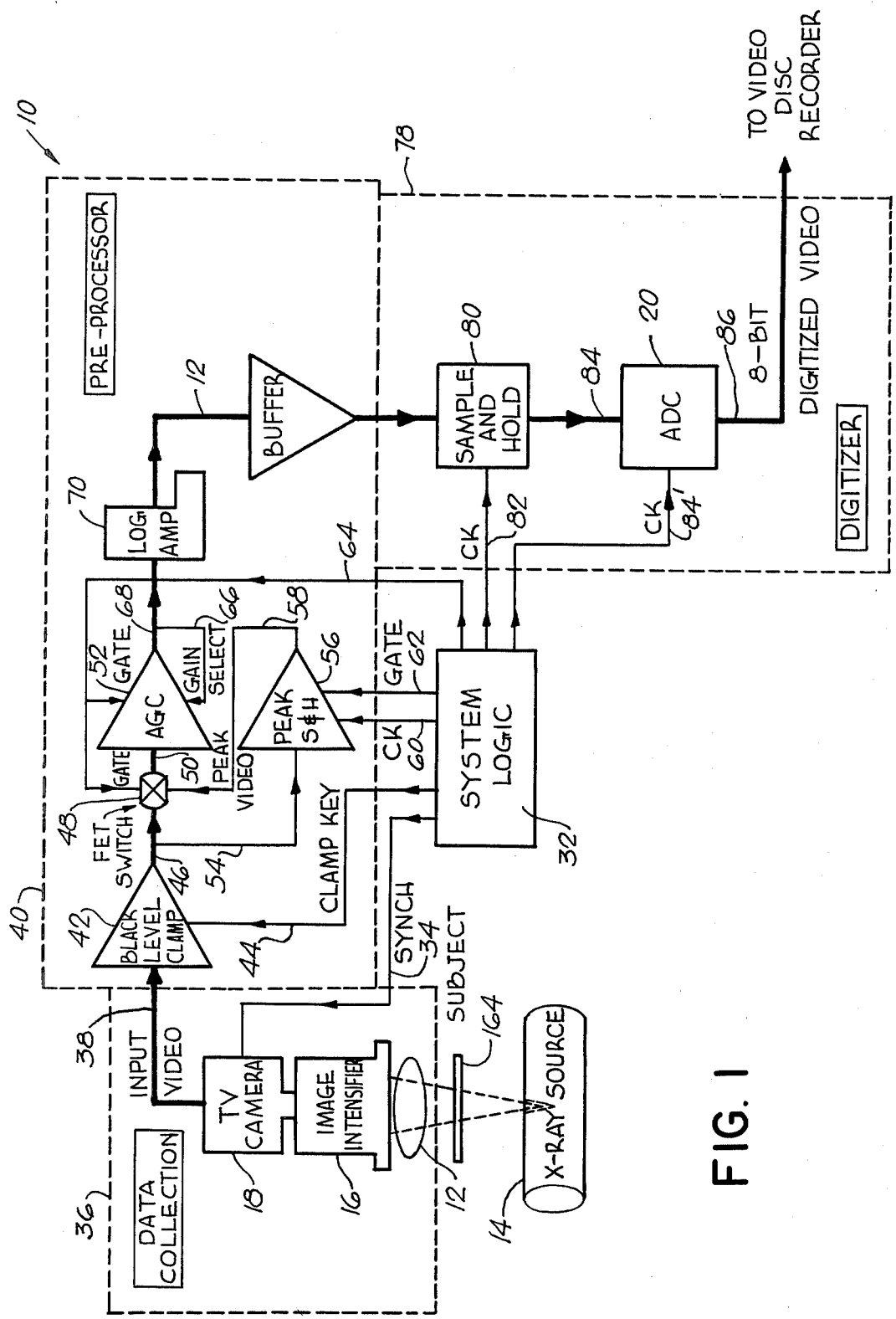
FIG. 1 is a schematic block diagram of X-ray apparatus illustrating the production of digital video signals corresponding with an X-ray image of a subject or patient.
Figure 2:
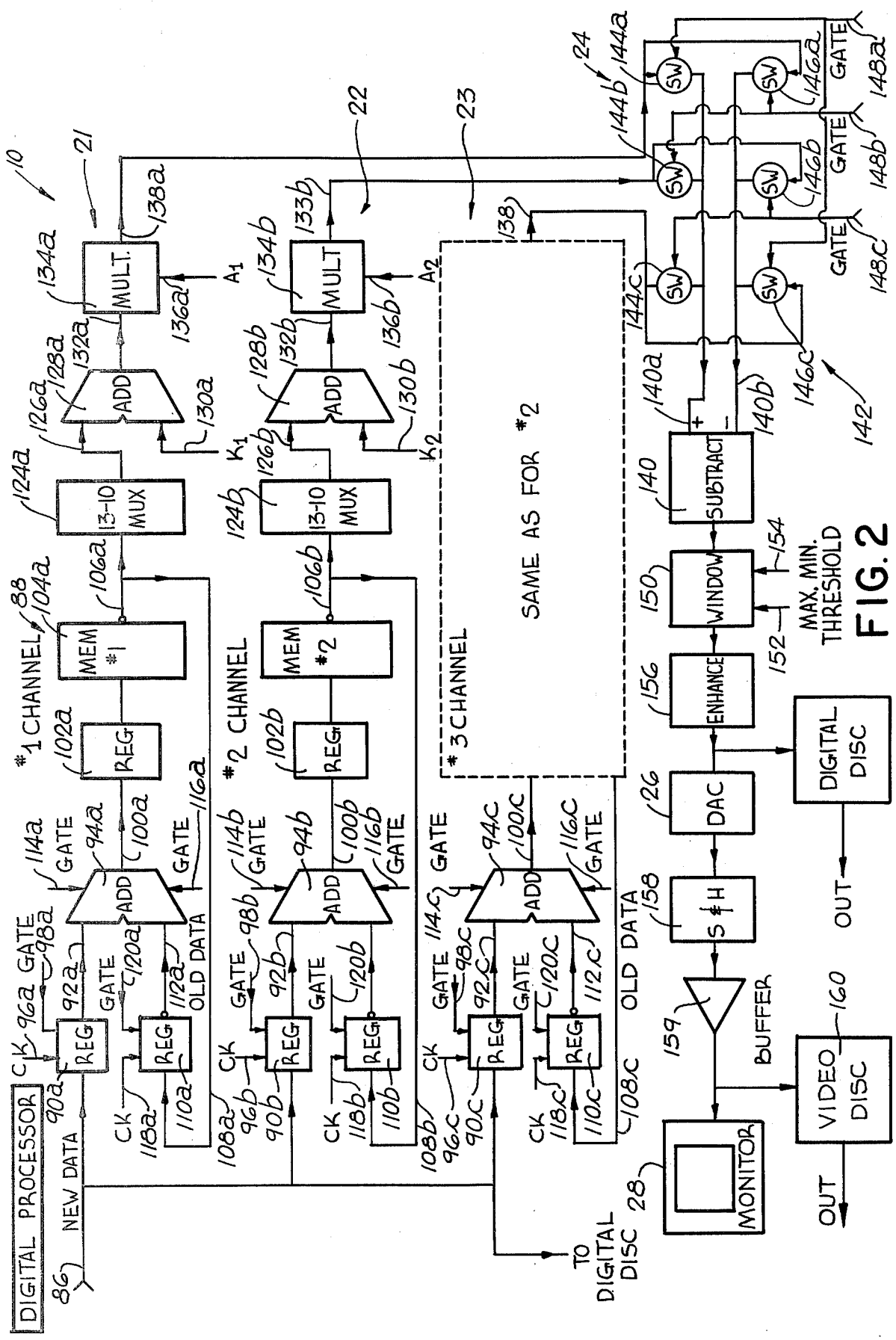
FIG. 2 is a schematic block diagram of apparatus illustrating the production of television difference images from the digital video signals in accordance with time interval differencing.

FIGS. 1-3 illustrate an embodiment of the present invention in the form of diagnostic anatomical X-ray apparatus 10 which will find many applications, but is particularly well adapted for producing a continuous series of images in real time to show any desired portion of the cardiovascular system of a patient or subject 12. Thus, for example, the X-ray apparatus 10 may be employed for visualizing the heart, with its associated arteries and veins, the various abdominal organs with the associated blood vessels, or the brain, with its associated arteries and veins.

The X-ray apparatus 10 is particularly well adapted for producing a continuous series of images in real time to show the motion of the heart. In carrying out such studies of the heart and other portions of the cardiovascular system, it generally is desirable to introduce an X-ray contrast medium, such as a composition containing iodine, into the cardiovascular system of the subject 12. There is no need for using a catheter, as in certain prior procedures, to introduce the contrast medium into a localized zone of the cardiovascular system. In one such prior procedure, it has been the practice to insert the catheter through an incision into a blood vessel, usually an artery, and to advance the catheter through the blood vessel to a location close to the heart, so that the contrast medium can be supplied through the catheter, directly to the heart. The use of a catheter results in a high concentration of the contrast medium in the heart. However, this procedure involves a significant hazard of producing an adverse reaction in the patient. It is much less hazardous to inject the contrast medium into a peripheral vein, without the use of a catheter. The X-ray apparatus of the present invention is capable of effectively visualizing the motion of the heart, with peripheral injection of the X-ray contrast medium, and without any need to use a catheter. Similarly, other portions of the cardiovascular system can be effectively visualized, with peripheral injection of the contrast medium, and without using a catheter.

The present invention, as represented by FIGS. 1-3, involves a method in which a continuous series of difference images are produced by integrating digital video signals over a series of successive time intervals, performing a series of subtractions between each set of integrated video signals and the preceding set and thereby producing a series of successive digital difference video signals, and converting such digital difference video signals into visible television difference images representing changes in the X-ray image between the successive time intervals. This method is particularly well adapted for visualizing the progress of a contrast medium injected into a peripheral portion of the cardiovascular system. However, useful difference images can also be produced without any injection of a contrast medium.

Generally, the diagnostic anatomical X-ray apparatus 10 of FIGS. 1-3 comprises means including an X-ray source or generator 14 for producing an anatomical X-ray image of the subject or patient 12, television means for converting such X-ray image into a continuous series of television fields comprising trains of analog video signals, such television means preferably including an image intensifier device 16 for producing a visible anatomical image corresponding with the X-ray image and a television camera 18 for converting the visible image into analog video signals, an analog-to-digital converter 20 for converting analog video signals into corresponding digital video signals, three digital memory systems 21, 22 and 23 for integrating and temporarily storing the digital video signals over a series of successive time intervals, subtracting means 24 for producing digital difference video signals by performing a series of subtractions between each set of integrated video signals and the preceding set of integrated video signals and thereby producing a series of successive digital difference video signals, a digital-to-analog converter 26 for converting the digital difference video signals into analog difference video signals, and means including a television display device 28 for producing visible difference images corresponding to the analog difference video signals and representing changes in the anatomical X-ray image between the successive time intervals. Preferably, an X-ray contrast medium is injected into the subject with a timing such that the contrast medium is moving in the field of view during the production of the difference images, so that the contrast medium is visualized in the difference images.

Generally, the three memory systems 21, 22 and 23 of FIG. 2 integrate the digital video signals over successive time intervals corresponding with a few television fields, such as four television fields, for example, which has the important advantage of greatly improving the signal-to-noise ratio of the digital video signals. However, the length of the integrating time intervals may be varied over a wide range, such as from two to sixty television fields, for example. The provision of three memory systems 21-23 makes it possible to produce a continuous television display on the display device or monitor 28. Each memory system in turn integrates and stores the incoming digital video signals, participates in a first subtraction operation in which the previously integrated video signals are subtracted from such integrated and stored video signals, and participates in a second subtraction operation in which such integrated and stored video signals are subtracted from the subsequently integrated video signals. Each memory system then integrates and stores a new set of digital video signals, so as to repeat the three part cycle. The digital difference video signals are supplied continuously to the digital-to-analog converter 26 which provides corresponding analog difference video signals for display by the television display device 28.

If each integrating interval is made equal to four television fields, the X-ray system 10 will produce fifteen complete difference images per second, based on a television field frequency of 60 hertz. Generally, the image resolution of the cardiovascular motion will suffer if the integrating interval of the memory systems 21-23 is made much greater than four television fields. On the other hand, the signal-to-noise ratio will suffer if the integrating interval is made less than four television fields.

Additional details of the X-ray system 10 are shown in FIGS. 1 and 2. The entire system is controlled by system logic or control means 32, which provides all of the control, timing and synchronizing pulses and signals for the entire system 10. Thus, the system logic 32 provides both horizontal and vertical synchronizing pulses for the television camera 18, as represented by a control line 34. The television synchronizing pulses are also provided for all other components of the television system, as needed.

The image intensifier and the TV camera 18 constitute data collection means 36, from which analog video signals are delivered along a signal line 38, extending to a preprocessor 40, which amplifies and processes the analog video signals. Initially, the analog video signals are transmitted through a black level clamp circuit 42, which clamps the black level of the television signals to ground or zero voltage. Clamp key pulses are supplied to the black level clamp circuit 42 from the system logic 32 along a line 44, to synchronize the operation of the black level clamp circuit 42 with the television fields.

The analog video signals are then transmitted along a line 46 to an F.E.T. switch 48, or any other suitable electronic switch, which selectively supplies the analog video signals along a line 50 to an automatic gain control circuit 52. The analog video signals from the black level clamp circuit are also supplied along a line 54 to a peak sample and hold circuit 56 which is involved in the operation of the automatic gain control circuit 52. The output of the circuit 56 is supplied along a line 58 to a second input of the electronic switch 48. The peak sample and hold circuit 56 is supplied with clock pulses and gate or control pulses by the system logic 32, over lines 60 and 62, whereby the operation of the circuit 56 is synchronized with the television fields. The system logic 32 also supplies vertical synch pulses along a line 64 to the automatic gain control circuit 52 and the electronic switch 48.

During each television field, the peak sample and hold circuit 56 samples and holds the peak video signal, and thus delivers the peak video signal to the line 58. During the vertical retrace between the television fields, the corresponding vertical synch pulse gates the switch 48, so that the input of the automatic gain control circuit is disconnected from the normal video line 46 and is connected to the peak video line 58. Thus, the peak video output of the circuit 56 is applied to the input of the automatic gain control circuit 52. At the same time, the automatic gain control circuit 52 is gated into its adjust mode by the vertical synch pulse, so that the output of the automatic gain control circuit is adjusted to a preselected desirable level. The output is fed back into the automatic gain control circuit 52 along a gain select line 66. With this circuit operation, the peak video signal for each television field selects the gain for the next television field.

The analog video signals from the automatic gain control circuit 52 are supplied along a line 68 to the input of a logarithmic amplifier 70, adapted to provide amplified output video signals which are proportional to the logarithm of the input video signal. It has been found that the provision of logarithmic amplification makes it possible to cancel out the background bone and soft tissue elements of the image when the mask image is subtracted from the subsequent images.

In this case, the output of the logarithmic amplifier 70 is supplied along a line 72 to a buffer amplifier 74, which provides amplified output signals to an output line 76, at a sufficiently high level for effective processing by a digitizer circuit 78.

As shown, the digitizer circuit 78 includes a sample and hold circuit 80 which receives the amplified analog video signals from the output line 76 of the buffer amplifier 74. The system logic 32 supplies clock pulses along a line 82 to the sample and hold circuit 80. The output of the sample and hold circuit 80 is supplied along a signal line 84 to the analog-to-digital converter (ADC) 20. The system logic 32 supplies clock pulses to the ADC 20 along a control line 84'. The ADC 20 converts the analog video signals into digital video signals, which are supplied to an output line 86. The digital output may be in the form of eight-bit digital signals, or in any other suitable form.

The sample and hold circuit 80 samples the analog video signals periodically, as determined by the clock pulses from the line 82, and holds the sampled analog value without change until the next clock pulse comes along. When the analog signal has been sampled and is being held, the sampled signal is digitized by the ADC 20. This circuit arrangement has the advantage that each sampled analog value is held constant while it is being digitized by the ADC 20, so that the analog value does not change during the digitizing process. This features makes it possible to digitize the analog video signals with a greater degree of accuracy.

The digital video line 86 also appears in FIG. 2, which illustrates digital processor circuits 88 for integrating, storing and subtracting the digital video signals, to provide digital difference video signals. As previously indicated, the circuits 88 preferably include the first, second and third memory systems or channels 21, 22 and 23. The digital video signals on the line 86 are supplied to the inputs of all three memory systems 21, 22 and 23, which are timed and controlled by pulses from the system logic control means 32.

All three memory systems 21–23 may be the same in construction. Thus, it will be sufficient to describe the first memory system 21 in detail. The digital video input line 86 is connected to the input of a register 90a having its output connected to one input 92a of an addition circuit 94a. Clock and gate or control pulses are supplied to the register 90a by the system logic 32 over clock and gate lines 96a and 98a.

The output of the addition circuit 94a is supplied along a line 100a to the input of a register 102a having its output connected to the input of a digital memory 104a, capable of storing the digital signals for at least one complete television field. While memories having various storage capacities may be employed, good results have been achieved with a digital memory having a storage capacity of 256×256×13. This storage capacity means that the digital memory 104a is capable of storing 13-bit digital words or values for 256 picture elements (pixels) for each of 256 television lines. This storage capacity amounts to 65,536 thirteen-bit digital words or values. The digital words are adapted to be circulated through the memory 104a and to be delivered successively to an output line 106a.

For the purpose of integration, the old data words from the output line 106a are supplied along a line 108a to the input of a register 110a having its output connected to a second input 112a of the addition circuit 94a. When the addition circuit 94a is processing data received from both input lines 92a and 112a, the two sets of data words are additively combined and are supplied to the output line 100a. Thus, the new digital video signals and the old or previously stored digital video signals are additively combined and are supplied to the input of the digital memory 104a for further storage. The additive processing of the data from the two input lines 92a and 112a is controlled by gate or control pulses supplied to the addition circuit 94a by the system logic 32 over gate pulse lines 114a and 116a. The system logic 32 supplies clock and gate or control pulses to the register 110a over clock and gate lines 118a and 120a.

As previously indicated, each of the three memory systems 21–23 is typically employed in turn to integrate and store the digital video signals during an integrating time interval which generally corresponds with a few television fields, such as four television fields, for example. On this basis, the gate pulses for the register 90a are timed so that this register transmits the new digital video signals throughout the first integrating time interval, and then ceases to transmit the digital video signals. The gate pulses for the old data register 110a are timed so that it transmits the old or previously stored digital video signals throughout the second and subsequent television fields of the first integrating time interval, and continuously thereafter during the remainder of the three part cycle.

The gate pulses for the addition circuit 94a are timed so that it additively combines the digital video signals from both input lines 92a and 112a during the second and subsequent television fields of the first integrating time interval, and then ceases to accept any input from the new data input line 92a, while containing to accept and transmit digital video signals from the old data input 112a. The registers 92a and 110a are clocked so that they supply the new and old digital video signals with the proper synchronization to the addition circuit 94a.

The register 102a is provided to supply the integrated digital video signals with the proper synchronization to the digital memory 104a, even though the pulses from the addition circuit 94a may deviate slightly from the proper synchronization. During each television field of the first integrating time interval, the new digital video signals are added to the recirculating, previously stored digital video signals, and the combined or integrated video signals are again fed into the digital memory 104a for storage therein. After the end of the first integrating time interval, the new digital video signals are no longer added, so that the previously stored digital video signals are simply recirculated through the memory 104a, the register 110a, the addition circuit 94a and the register 102a. During each television field of the three part cycle after the first integrating time interval, the integrated video signals appear at the output line 106a of the digital memory 104a and are supplied to the subtraction means 24, after some further processing.

To provide such further processing, the first memory system 21 comprises a thirteen-ten multiplexer 124a which converts or normalizes the 13-bit digital words into 10-bit words, incorporating the most significant bits of the 13-bit words. The output line 106a from the digital memory 104a is connected to the input of the 13-10 multiplexer 124a. The ten-bit output words from the multiplexer 124a are supplied to one input 126a of an addition circuit 128a, which is provided for the purpose of adding a variable constant $K_1$ to the 10-bit digital video signals. The system logic 32 supplies the constant $K_1$ to the second input of the addition circuit 128a over a line 130a. The constant $K_1$ is in the form of a ten-bit digital word which can be selected by the operator. If no constant needs to be added, the operator simply enters zero as the constant $K_1$. The ability to add a constant makes it possible to adjust the digital video signals for the best possible subtraction by the subtraction unit 24.

The output of the addition unit 128a is supplied to one input 132a of a multiplication circuit 134a, having a second input 136a which is supplied with a coefficient $A_1$ by the system logic 32. The coefficient $A_1$ is in the form of a digital word which can be selected by the operator. If no multiplication is needed, the coefficient is selected as 1. However, the ability to introduce a coefficient makes it possible to adjust the digital video signals for the best possible subtraction by the subtraction circuit 24.

As previously indicated, the second and third memory systems 22 and 23 may be the same in construction as the first memory system 21. In FIG. 2, the various components of the second and third memory systems have been identified with the same reference characters as employed for the corresponding components of the first memory system 21, with the addition of the suffixes b and c, instead of a. Thus, the second and third memory systems 22 and 23 have output lines 138b and c which are connected to the subtraction means 24.

In the time interval differencing method of FIG. 2, digital video signal are integrated in turn by the three memory systems 21-23, over a series of successive time intervals corresponding with a plurality of television fields. In this way, a series of sets of integrated digital video signals are produced. Preferably, three successive sets of integrated digital video signals are produced in rotation. Generally, the successive sets of integrated digital video signals are integrated over time intervals which are approximately equal, usually corresponding with a few television fields, such as four television fields, for example. The principal purpose of the integration is to improve the signal-to-noise ratio. The interval of integration may be varied over a wide range, as desired, from 2 to 60 television fields, at least, for example.

In the time interval differencing method of FIG. 2, successive subtractions are performed in rotation between each set of integrated digital video signals and the preceding set of integrated digital video signals, so as to produce a series of successive digital difference video signals, which are converted into analog difference video signals. Finally, such analog difference video signals are employed to produce a visible display of television difference images, representing the changes in the X-ray image between the successive time intervals.

As previously indicated, it is preferred to produce three successive sets of integrated digital video signals in rotation. In this preferred version of time interval differencing, the first set of integrated digital video signals is subtracted from the second set, the second set from the third, the third from the first, and so forth. This method of time interval differencing has the advantage that a continuous display of television difference images can readily be produced.

In the illustrative apparatus of FIG. 2, the subtraction means may comprise a subtraction circuit 140 having an add input 140a and a subtract input 140b. Digital video signals supplied to the subtract input 140b are subtracted from digital video signals supplied to the add input 140a. The subtraction means 24 may comprise an electronic switching matrix or means 142, connected between the three output lines 138a, b and c and the input lines 140a and b of the subtraction circuit 140. It will be recalled from the previous description that the output lines 138a, b and c are connected to the outputs of the three memory systems 21, 22 and 23.

The electronic switching matrix 142 of FIG. 2 comprises three electronic switches 144a, b and c which are connected between the respective output lines 138a, b and c and the add input 140a of the subtraction circuit 140. In addition, the electronic switching matrix 142 comprises three electronic switches 146a, b and c, which are connected between the output lines 138a, b and c and the subtract input 140b of the subtraction circuit 140. The electronic switches 144a, b and c are activated in rotation by timing or control pulses supplied from the system logic 32 over gate lines 148a, b and c, respectively. The control pulses supplied over the gate lines 148a, b and c are also employed to activate the electronic switches 146a, b and c, but the sequence is offset or staggered by one step. Thus, the second stage line 148b is connected to the first electronic switch 146a associated with the first output line 138a. The third gate line 148c is connected to the second electronic switch 146b. The first gate line 148a is connected to the third electronic switch 146c.

At its output, the subtraction circuit 140 produces digital difference video signals which may be subjected to additional processing before being supplied to the digital-to-analog converter 26. Thus, in the apparatus of FIG. 2, the output of the subtraction circuit 140 is supplied to the input of a window or threshold circuit 150, which preferably establishes adjustable minimum and maximum thresholds, as determined by adjustable control signals supplied by the system logic 32 to maximum and minimum threshold control lines 152 and 154 connected to the window circuit 150. Thus, all of the digital video signals below the minimum threshold will be rendered or displayed as black, while all of the digital video signals above the maximum threshold will be rendered or displayed as white.

In the apparatus of FIG. 2, the output of the window circuit 150 is connected to the input of an adjustable enhance circuit 156, which reduces the number of bits in the digital difference video signals and selectively determines whether the bits transmitted to the DA converter 26 will be derived from the lower order or higher order bits of the input signals. For example, the input digital video signals to the enhance circuit 156 may have nineteen bits, while the output signals may have ten bits, to match the desired number of input bits for the DA converter 26. The enhance circuit 156 can be adjusted to slide the selected group of ten bits anywhere along the nineteen bit input scale. If the ten bits of the lowest order are selected, the contrast at the black end of the television scale will be enhanced. The presence of nineteen bits at the input to the enhance circuit 156 is due to the multiplication operations in the multiplication circuits 134a, b and c. As previously indicated, the input digital video signals to the multiplication circuits 134a, b and c may contain ten bits. If the coefficients $A_1$, $A_2$ and $A_3$ contain nine bits, the digital output video signals from the multiplication circuits 134a, b and c will contain nineteen bits in each digital word. The numbers of bits are given by way of example and may be varied, as desired.

The digital difference video signals from the output of the enhance circuit 156 are supplied to the input of the digital-to-analog converter 26, which converts the digital difference video signals into analog difference video signals. The analog output of the DA converter 26 is supplied to a sample and hold circuit 158 which removes minor oscillations or transients which are introduced by the DA converter 26. Such oscillations or transients tend to occur at the beginning of each analog signal component corresponding to each digital word which is converted by the DA converter 26. The sample and hold circuit 158 is able to remove such oscillations by sampling and holding the successive analog components or values, after the oscillations have died out. Thus, smoother analog video signals are produced at the output of the sample and hold circuit 158.

The analog difference video signals at the output of the sample and hold circuit 158 are amplified by a buffer amplifier 159 having its output connected to the television display device or monitor 28. Thus, the television monitor 28 produces a continuous series of visible difference images, representing the difference between the current X-ray image and the previous X-ray image which existed during the preceding time interval. The subtraction of the previous image cancels out the image elements due to bone and soft tissue, so that the remaining difference image elements represent primarily any changes in the X-ray contrast medium.

In the difference images displayed by the television monitor 28, the movement of the X-ray contrast medium in the heart and circulatory system of the subject is clearly visible. Thus, abnormalities in the functioning of the heart are rendered visible. If the three memory systems 21-23 are operated so as to integrate the video signals over four television fields, the television monitor 28 will produce fifteen different images per second, based on a television field frequency of 60 Hertz. Each image is produced four times before the next image is produced. The production of fifteen images per second is sufficient to show the action of the heart clearly, for accurate diagnosis of abnormal conditions.

If desired, the analog difference video signals from the output of the buffer amplifier 159 may also be supplied to a video disc recorder 162, so that the video signals can be recorded and played back repeatedly through the monitor 28.

If desired, a digital video disc recorder 162 may be employed, for recording the digital difference video signals at the output of the enhance circuit 156, or the raw digital video signals from the line 86. If the digital difference video signals are recorded by the digital disc recorder 162, the output of the recorder can subsequently be connected to the input of the DA converter, so that the recorded signals can be repeatedly displayed on the television display device 28. If the raw digital video signals are recorded, they can be subsequently reprocessed by connecting the output of the digital video disc recorder 162 to the line 86, so that the raw digital video signals will again be supplied to the inputs of the memory systems 21, 22 and 23. If desired, the memory systems 21, 22 and 23 can be readjusted to change the processing of the digital video signals. For example, the integratng time intervals of the memory systems 21, 22 and 23 can be changed by changing the timing pulses supplied by the system logic 32. It is also possible to change any of the constants $K_1$, $K_2$ and $K_3$ or the coefficients $A_1$, $A_2$ and $A_3$, or both.

In describing the operation of the apparatus of FIGS. 1 and 2, it will be assumed for clarity that the integrating interval of each memory system is four television fields, although the integrating interval may be varied, as desired. The control signals supplied by the system logic 32 are timed so that the three memory systems 21, 22 and 23 integrate the digital video signals from the input line 86 for successive intervals of four television fields.

The sequence is summarized in FIG. 3. Thus, for the first four television fields, the first memory system 21 is supplied with new digital video signals by the new data input register 90a. After the first four television fields, the register 90a is shut down by its gating pulses from the system logic 32. For the next eight television fields, the integrated and stored digital video signals in the first memory system 21 simply recirculate, and thus are available for transmission to the subtraction circuit 142a by the electronic switches 144a and 146a. During television frames 5-8, the first integrated digital video signals are transmitted by the electronic switch 144a to the add input 140a of the subtraction circuit 140. During the television fields 9-12, the first integrated digital video signals are supplied by the electronic switch 146a to the subtract input 140b of the subtraction circuit 140.

During television fields 13–16, the new data input register 90a of the first memory system 21 is again activated, so that the new digital video signals are again integrated in the first memory system 21. During television field 13, the previously stored data in the first memory system 21 is not recirculated, and thus is cancelled. This is easily accomplished by timing the control pulses from the system logic 32 so as to shut down the recirculation register 110a during television field 13. The register 110a is again activated during television fields 14–16, and remains activated for eight television fields thereafter.

For television fields 5–8, constituting the second set of four fields, the new digital video signals are integrated and stored in the second memory system 22. During the next eight fields 9–16, the new data input register 90b is shut down, so that the integrated and stored digital video signals are circulated in the second memory system 22. During television fields 9–12, the second integrated digital video signals are transmitted to the add input 140a of the subtraction circuit 140 by the electronic switch 144b. During the television fields 13–16, the second integrated digital video signals are transmitted to the subtract input 140b of the subtraction circuit 140 by the electronic switch 146b.

This cycle, lasting twelve television fields, is repeated during the next twelve television fields and each subsequent interval of twelve television fields. During the first field of each twelve-field cycle, the data stored in the second memory system 22 is not recirculated and thus is discarded, so that only the new digital video signals are integrated.

The third memory system 23 also goes through successive twelve-field cycles. During the first four fields 9–12, the new digital video signals are admitted through the new data input register 90c and are integrated and stored in the third memory system 23. During the next eight television fields 13–20, the input register 90c is shut down by its control signals from the system logic 32, but the third digital video signals are recirculated. During television fields 13–16, the third integrated digital video signals are transmitted through the electronic switch 144c to the add input 140a of the subtraction circuit 140. During television frames 17–20, the third integrated digital video signals are transmitted through the electronic switch 146c to the subtract input 140b of the subtraction circuit 140. This twelve-field cycle is repeated during each subsequent interval of twelve television fields. During the first field of each cycle, the previously integrated and stored data is not recycled and thus is discarded.

After the first eight television fields, during which the first and second memory systems 21 and 22 are being loaded with integrated digital video signals, the entire apparatus represented by FIG. 3 goes through a series of successive twelve-field subtraction cycles. During television fields 9–12, the first integrated digital video signals stored in the first memory system 21 are subtracted from the second integrated digital video signals stored in the second memory system 22, to produce difference video signals which are displayed on the television display device 28. A difference image is thus produced, in which the unchanging image elements are cancelled out. The difference image represents the differences or changes in the X-ray image between the two successive time intervals. A difference image is displayed four times during television fields 9–12.

During television fields 13–16, the second integrated digital video signals from the second memory system 22 are subtracted from the third integrated digital video signals from the third memory system 23, to produce another set of digital difference video signals. A corresponding difference image is displayed by the television display device 28. This image is displayed four times during television fields 13–16. During television fields 17–20, the third integrated digital video signals from the third memory system 23 are subtracted from the first integrated digital video signals from the first memory system 21, to produce a third set of digital difference video signals. A corresponding difference image is displayed four times by the television display device 28 during television fields 17–20. The twelve-field subtraction cycle is then repeated during each subsequent twelve-field cycle.

The apparatus 10 represented by FIGS. 1–3 thus produces a continuous series of difference images, representing the progressive changes in the X-ray image. The difference images displayed by the display device 28 represent approximately the first derivative of the X-ray image. In the human or other anatomical subject 12 of FIG. 1, the image elements due to bone and soft tissue are largely unchanging, and thus are largely cancelled out in the difference images. However, any movement, such as heart movement, is preserved in the difference images. Thus, time interval differencing, as represented by FIGS. 1–3, is advantageous for its ability to visualize heart movement, without being obscured by unchanging bone and soft tissue.

While heart movement can be visualized without the use of an X-ray contrast medium, it is often advantageous to increase the degree of visualization by introducing an X-ray contrast medium into the anatomical subject 12, with a timing such that the contrast medium becomes operative during the time interval differencing. It is not necessary to insert a catheter to introduce the contrast medium near the heart. Instead, the contrast medium can simply be injected peripherally into one or more veins in the arms or legs of the subject. The peripheral injection of the X-ray contrast medium eliminates the hazard which is associated with the insertion of a catheter into the circulatory system.

The X-ray contrast medium may take the form of a composition containing iodine. In that case, it is advantageous to employ an X-ray filter 164 containing cerium in the path of the X-rays from the source 14. The cerium filter increases the contrast produced by the iodine composition, due to the interplay between the K-edge absorption characteristics of cerium and iodine.

In time interval differencing, as represented by FIGS. 1–3, each stored set of digital video signals serves as a mask for a subsequent set of stored video signals.

It will be understood that the integrating interval in time interval differencing can be varied from two television fields upwardly. Moreover, time interval differencing can be employed without integration. In that case, each of the three memory systems 21–23 is simply employed to store the digital video signals for a single television field. Each stored set of digital video signals is then subtracted from the next set. However, in the absence of integration, the resulting difference images will suffer from a lower signal-to-noise ratio.

In the X-ray apparatus 10 of FIGS. 1–3, the video disc recorder 160 can also be employed to record the raw analog video signals. For this purpose, the video disc recorder is connected to the output line 76 for the buffer amplifier 74, as indicated in FIG. 1. After each run, the analog video signals can be played back into the line 76 and reprocessed through the AD converter 20, the memory systems 21, 22 and 23, the subtraction means 24, the DA converter 26 and the television display device 28. For reprocessing, the memory systems 21, 22 and 23 can be adjusted differently than in the original run.

Similarly, the raw digital video signals on the line 86 can be recorded on the digital disc recorder 162. After each run, the recorded digital video signals can be played back into the line 86 and reprocessed.

During reprocessing, the integrating time interval can be changed, as desired. Moreover, the memory systems 21–23 can be readjusted. By thus reprocessing the recorded video signals, various portions of the circulatory system, with the X-ray contrast medium therein, can sometimes be visualized even more clearly than in the original run.

Any known or suitable X-ray contrast medium may be employed in connection with the described methods. Alternatively, the described methods may be employed without using any contrast medium.

X-ray filtration may be employed, with or without the use of a contrast medium. The X-ray filter may advantageously contain cerium when a contrast medium containing iodine is used. However, the X-ray filter may be of any known or suitable composition, adapted to enhance the visibility of the physiological features to be examined.

Instead of cerium, the X-ray filter may contain another suitable element having a k-shell absorption edge between 40 and 60 k.e.v.

We claim:

1. A method of producing visible difference images derived from an X-ray image of an anatomical subject, comprising the steps of directing X-rays through an anatomical subject to produce an X-ray image, converting said X-ray image into series of television fields comprising trains of analog video signals, converting said analog video signals into corresponding digital video signals, integrating said digital video signals over a series of successive time intervals each corresponding with a plurality of successive television fields and thereby producing a series of successive separate sets of integrated digital video signals, performing a series of successive subtractions between each successive separate set of integrated video signals and the immediately preceding set of integrated video signals and thereby producing a series of successive separate sets of digital difference video signals, converting said digital difference video signals into analog difference video signals, and converting said analog difference video signals into a series of successive visible television difference images representing changes in the X-ray image between the successive time intervals.

2. A method according to claim 1, in which each of said time intervals is on the order of four consecutive television fields.

3. A method according to claim 1, including the step of providing filtration of the X-rays to enhance the visibility of an X-ray contrast medium.

4. A method according to claim 1, including the step of producing filtration of the X-rays with a filter medium containing cerium to enhance the visibility of an X-ray contrast medium containing iodine.

5. A method according to claim 1, including the step of introducing an X-ray contrast medium into the anatomical subject with a timing such that movement of the contrast medium in the subject will occur during the series of television fields.

6. A method according to claim 5, including the step of producing filtration of the X-rays to enhance the visibility of the X-ray contrast medium.

7. A method according to claim 1, including the step of introducing an X-ray contrast medium containing iodine into the anatomical subject with a timing such that movement of the contrast medium in the subject will occur during the series of television fields.

8. A method according to claim 7, including the step of producing filtration of the X-rays with a filter medium containing cerium to enhance the visibility of the iodine.

9. A method according to claim 1, including the step of logarithmically amplifying the analog video signals prior to the conversion to digital signals.

10. Diagnostic anatomical X-ray apparatus, comprising
means including an X-ray source for producing an anatomical X-ray image,
television means for converting said X-ray image into a series of television fields comprising trains of analog video signals,
an analog-to-digital converter for converting said analog video signals into corresponding digital video signals,
three memory systems for successively storing said digital video signals,
cyclical means for successively supplying said digital video signals to said three memory systems in rotation for successive first, second and third time intervals,
each of said memory systems comprising a digital memory having a capacity corresponding to at least one television field and integrating means for causing said digital memory to integrate said digital video signals over a predetermined number of successive television fields for the corresponding time interval,
subtracting means for producing digital difference video signals by performing a subtraction between the two sets of integrated digital video signals stored in the most recently filled memory system and the previously filled memory system during the time interval when the other memory system is being filled,
a digital-to-analog converter for converting said digital difference video signals into analog difference video signals,
and means including a television display device for producing visible difference images corresponding to said analog difference video signals and representing changes in the anatomical X-ray image between the successive time intervals.

11. Diagnostic anatomical X-ray apparatus according to claim 10,
including means for establishing each of said time intervals so as to be on the order of four successive television fields.

12. Diagnostic anatomical X-ray apparatus according to claim 10,
comprising means for establishing each of said time intervals to correspond with a plurality of complete successive television fields.

13. Diagnostic anatomical X-ray apparatus according to claim 10,
comprising X-ray filtration means between said X-ray source and said television means for enhancing the visibility of a predetermined X-ray contrast medium.

14. Diagnostic anatomical X-ray apparatus according to claim 10,
comprising X-ray filtration means between said X-ray source and said television means,
said X-ray filtration means containing cerium for enhancing the visibility of an X-ray contrast medium containing iodine.

15. Diagnostic anatomical X-ray apparatus according to claim 10,
including a logarithmic amplifier for logarithmically amplifying said analog video signals for presentation to said analog-to-digital converter.

16. Diagnostic anatomical X-ray apparatus according to claim 10,
in which said television means includes an image intensifier device for producing a visible anatomical image corresponding with said X-ray image, and a television camera for converting said visible image into a series of television fields comprising trains of analog video signals.

17. A method according to claim 1,
including the step of producing filtration of the X-rays with a filter medium containing an element having a k-shell absorption edge between 40 and 60 k.e.v. to enhance the visibility of an X-ray contrast medium containing iodine.

18. A method according to claim 7,
including the step of producing filtration of the X-rays with a filter medium containing an element having a K-shall absorption edge between 40 and 60 k.e.v. to enhance the visibility of the iodine.

19. Diagnostic anatomical X-ray apparatus according to claim 10,
comprising X-ray filtration means between said X-ray source and said television means,
said X-ray filtration means containing an element having a k-shell absorption edge between 40 and 60 k.e.v. for enhancing the visibility of an X-ray contrast medium containing iodine.

20. A method of producing visible difference images derived from an X-ray image of an anatomical subject,
comprising the steps of directing X-rays through an anatomical subject to produce an X-ray image,
converting said X-ray image into a series of television fields comprising trains of analog video signals,
converting said analog video signals directly into corresponding digital video signals in real time without any intervening analog storage,
integrating said digital video signals in real time over a series of successive time intervals each corresponding with a plurality of successive television fields and thereby producing a series of successive separate sets of integrated digital video signals,
performing a series of successive subtractions in real time between each successive set of integrated video signals and the immediately preceding set of integrated video signals and thereby producing a series of successive separate sets of digital difference video signals,
converting said digital difference video signals in real time into analog difference video signals,
and converting said analog difference video signals in real time into a series of successive visible television difference images representing changes in the X-ray image between the successive time intervals.

21. Diagnostic anatomical X-ray apparatus,
comprising means including an X-ray source for producing an anatomical X-ray image,
television means for converting said X-ray image into a series of television fields comprising trains of analog video signals,
an analog-to-digital converter connected directly to said television means for converting said analog video signals into corresponding digital video signals in real time,
three memory systems for successively storing said digital video signals in real time,
cyclical means for successively supplying said digital video signals from said converter to said three memory systems in rotation in real time for successive first, second and third time intervals,
each of said memory systems comprising a digital memory having a capacity corresponding to at least one television field and integrating means for causing said digital memory to integrate said digital video signals in real time over a predetermined number of successive television fields for the corresponding time interval,
subtracting means for producing digital difference video signals by performing a subtraction in real time between the two sets of integrated digital video signals stored in the most recently filled memory system and the previously filled memory system during the time interval when the other memory system is being filled,
a digital-to-analog converter for converting said digital difference video signals in real time into analog difference video signals,
and means including a television display device for producing visible difference images in real time corresponding to said analog difference video signals and representing changes in the anatomical X-ray image between the successive time intervals.

22. Diagnostic anatomical X-ray apparatus,
comprising means including an X-ray source for producing an anatomical X-ray image,
television means for converting said X-ray image into a series of television fields comprising trains of analog video signals,
an analog-to-digital converter for converting said analog video signals in real time into corresponding digital video signals,
three memory systems for successively storing said digital video signals in real time,
cyclical means for successively supplying said digital video signals in real time to said three memory systems in rotation for successive first, second and third time intervals, each of said intervals corresponding with at least one television field.

each of said memory systems comprising a digital memory having a capacity corresponding to at least one television field, subtracting means for producing digital difference video signals by performing a subtraction in real time between the two sets of digital video signals stored in the most recently filled memory system and the previously filled memory system during the time interval when the other memory system is being filled, a digital-to-analog converter for converting said digital difference video signals in real time into analog difference video signals, and means including a television display device for producing visible difference images in real time corresponding to said analog difference video signals and representing changes in the anatomical X-ray image between the successive time intervals.

23. A method of producing visible difference images derived from an X-ray image of an anatomical subject, comprising the steps of directing X-rays through an anatomical subject to produce an X-ray image, converting said X-ray image into a series of television fields comprising trains of analog video signals, converting said analog video signals into corresponding digital video signals, performing a first integrating cycle by integrating said digital video signals over first, second and third successive time intervals each corresponding with a plurality of successive television fields and thereby producing first, second and third successive separate sets of integrated digital video signals, performing a series of successive integrating cycles which are substantially the same as said first integrating cycle, repetitively performing a series of successive subtractions between (a) the second and first sets of integrated digital video signals of each cycle, (b) the third and second sets of integrated digital video signals of each cycle, and (c) the first set of integrated digital video signals of the second and subsequent cycles and the third set of integrated digital video signals of the immediately preceding cycle and thereby producing a repetitive series of successive separate sets of digital difference video signals, converting said digital difference video signals into corresponding analog difference video signals, and converting said analog difference video signals into a series of successive visible television difference images representing changes in the X-ray image between the successive time intervals.

24. A method according to claim 23, in which each of said time intervals is on the order of four successive television fields.

25. A method according to claim 23, including the step of providing filtration of the X-rays to enhance the visibility of an X-ray contrast medium.

26. A method according to claim 23, including the step of producing filtration of the X-rays with a filter medium containing cerium to enhance the visibility of an X-ray contrast medium containing iodine.

27. A method according to claim 23, including the step of introducing an X-ray contrast medium into the anatomical subject with a timing such that movement of the contrast medium in the subject will occur during the series of television fields.

28. A method according to claim 27, including the step of producing filtration of the X-rays to enhance the visibility of the X-ray contrast medium.

29. A method according to claim 23, including the step of introducing an X-ray contrast medium containing iodine into the anatomical subject with a timing such that movement of the contrast medium in the subject will occur during the series of television fields.

30. A method according to claim 29, including the step of producing filtration of the X-rays with a filter medium containing cerium to enhance the visibility of the iodine.

31. A method according to claim 23, including the step of logarithmically amplifying the analog video signals prior to the conversion to digital signals.

32. A method according to claim 23, including the step of producing filtration of the X-rays with a filter medium containing an element having a k-shell absorption edge between 40 and 60 k.e.v. to enhance the visibility of an X-ray contrast medium containing iodine.

33. A method according to claim 29, including the step of producing filtration of the X-rays with a filter medium containing an element having a k-shell absorption edge between 40 and 60 k.e.v. to enhance the visibility of the iodine.

34. A method of producing visible difference images derived from an X-ray image of an anatomical subject, comprising the steps of directing X-rays through an anatomical subject to produce an X-ray image, converting said X-ray image into a series of television fields comprising trains of analog video signals, converting said analog video signals directly into corresponding digital video signals in real time without any intervening analog storage, performing a first integrating cycle by integrating said digital video signals in real time over first, second and third successive time intervals each corresponding with a plurality of successive television fields and thereby producing first, second and third successive separate sets of integrated digital video signals, performing a series of successive integrating cycles which are substantially the same as said first integrating cycle, repetitively performing a series of successive subtractions in real time between (a) the second and first sets of integrated digital video signals of each cycle, (b) the third and second sets of integrated digital video signals of each cycle, and (c) the first set of integrated digital video signals of the second and subsequent cycles and the third set of integrated digital video signals of the immediately preceding cycle and thereby producing a repetitive series of successive separate sets of digital difference video signals, converting said digital difference video signals in real time into corresponding analog difference video signals, and converting said analog difference video signals in real time into a series of successive visible television difference images representing changes in the X-ray image between the successive time intervals.

35. A method of producing visible difference images derived from an X-ray image of an anatomical subject, comprising the steps of directing X-rays through an anatomical subject to produce an X-ray image, converting said X-ray image into a series of television fields comprising trains of analog video signals, converting said analog video signals directly into corresponding digital video signals in real time without any intervening analog storage, performing a first storage cycle by storing said digital video signals in real time over first, second and third successive time intervals each corresponding with at least one television field and thereby producing first, second and third successive separate sets of stored digital video signals, performing a series of successive storage cycles which are substantially the same as said first storage cycle, repetitively performing a series of successive subtractions in real time between (a) the second and first sets of stored digital video signals of each cycle, (b) the third and second sets of stored digital video signals of each cycle, and (c) the first set of stored digital video signals of the second and subsequent cycles and the third set of stored digital video signals of the immediately preceding cycle and thereby producing a repetitive series of successive separate sets of digital difference video signals, converting said digital difference video signals in real time into analog difference video signals, and converting said analog difference video signals in real time into a series of successive visible television difference images representing changes in the X-ray image between the successive time intervals.

* * * * *

UNITED STATES PATENT AND TRADEMARK OFFICE
CERTIFICATE OF CORRECTION

PATENT NO. : 4,204,226
DATED : May 20, 1980
INVENTOR(S) : Mistretta, Kruger and Houk It is certified that error appears in the above-identified patent and that said Letters Patent are hereby corrected as shown below:

Column 6, line 5, "features" should be -- feature --

Column 7, line 10, "containing" should be --continuing --

Column 8, line 7, "signal" should be -- signals --

Column 9, line 1, "stage" should be -- gate --

Signed and Sealed this

Twenty-eighth Day of October 1980

[SEAL]

Attest:

SIDNEY A. DIAMOND

Attesting Officer

Commissioner of Patents and Trademarks